United States Patent [19]

Moreton

[11] Patent Number: 5,780,403
[45] Date of Patent: Jul. 14, 1998

[54] ASH-FREE DETERGENTS THEIR PREPARATION AND USE IN LUBRICATING OIL COMPOSITIONS

[75] Inventor: David J. Moreton, Hull, United Kingdom

[73] Assignee: BP Chemicals (Additives) Limited, London, England

[21] Appl. No.: 597,184

[22] Filed: Feb. 6, 1996

[30] Foreign Application Priority Data

Feb. 15, 1995 [GB] United Kingdom .................... 9502972

[51] Int. Cl.⁶ .................... C10M 133/00; C10M 133/22; C10M 129/16; C07C 43/11
[52] U.S. Cl. .................... 508/580; 568/609; 568/631; 568/632; 568/633; 568/640; 568/644
[58] Field of Search .................... 508/580; 568/609, 568/631, 632, 633, 640, 644

[56] References Cited

U.S. PATENT DOCUMENTS

| | | | |
|---|---|---|---|
| 5,043,415 | 8/1991 | Harris et al. | 568/631 |
| 5,114,601 | 5/1992 | Cook et al. | 568/631 |
| 5,205,946 | 4/1993 | Cook et al. | 568/631 |
| 5,589,445 | 12/1996 | Leahy et al. | 508/381 |
| 5,602,084 | 2/1997 | Moreton | 508/391 |

FOREIGN PATENT DOCUMENTS

| | | |
|---|---|---|
| 0 450 874 A2 | 10/1991 | European Pat. Off. . |
| 264 446 A1 | 2/1989 | Germany . |

OTHER PUBLICATIONS

R. Ungaro et al. "Molecular Inclision in functionalized . . . " Jour of Inclusion Phenomena, vol. 3, 1985, pp. 35–42.
V. Bocchi et al. "Synthesis iH NMR, 13C NMR spectra . . . " Tetraherdon, vol. 38 No. 3, 1982, pp. 373–378.

*Primary Examiner*—Jerry D. Johnson
*Attorney, Agent, or Firm*—Nixon & Vanderhye

[57] ABSTRACT

A compound comprised of a moiety derived from an organic nitrogen-containing base and a calixarene moiety in which the hydroxyl substituent (or substituents) is (are) substituted by oligoether chains. Typically, the compounds are complexes of the formula (I):

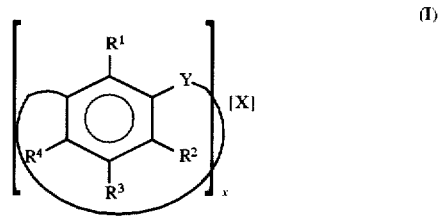

wherein Y is a divalent bridging group;

$R^3$ is hydrogen, hydrocarbyl or a hetero-substituted hydrocarbyl group;

either (1) $R^1$ is $OR^5$ and $R^2$ and $R^4$ are independently either hydrogen, hydrocarbyl or hetero-substituted hydrocarbyl, or (2) $R^1$ is either hydrogen, hydrocarbyl or hetero-substituted hydrocarbyl, and either both $R^2$ and $R^4$ are $OR^5$ or one of $R^2$ and $R^4$ is $OR^5$ and the other is —OH, $R^5$ being —$(Z)_nR^6$ in which Z is at least one alkylene oxide group, $R^6$ is hydrocarbyl or hetero-substituted hydrocarbyl and n is an integer in the range from 1 to 10; x is an integer in the range from 3 to 12; and X is a moiety derived from an organic nitrogen-containing base.

10 Claims, No Drawings

ASH-FREE DETERGENTS THEIR PREPARATION AND USE IN LUBRICATING OIL COMPOSITIONS

The present invention relates to lubricating oil additives and in particular to ash-free additives which function as detergents in lubricating oils, their preparation and use.

In the internal combustion engine, by-products from the combustion chamber often blow by the piston and admix with the lubricating oil. This is particularly marked in diesel engines operating on low-grade fuels of high sulphur content wherein corrosive acids are produced by combustion. The acids thereby incorporated in the lubricating oil can include sulphur acids produced by oxidation of sulphur, hydrohalic acids derived from halogen lead scavengers in the fuel and nitrogen acids produced by the oxidation of atmospheric nitrogen within the combustion chamber. Such acids cause deposition of sludge and corrosion of bearings and engine parts leading to rapid wear and early breakdown of the engine.

Compounds generally employed to neutralise the acidic materials and disperse sludge within the lubricating oil include metal, particularly alkaline earth metal, hydrocarbyl phenates, sulphonates, salicylates and napthenates, which materials are generally referred to as detergents.

Whilst the aforesaid materials function perfectly satisfactorily as detergents, from the environmental point of view they suffer from the disadvantage that they contain metals and on combustion result in the formation of ash. Increasing environmental awareness is prompting a search for metal-free or ash-free detergents. In pursuit of this objective we have found that certain compounds of organic nitrogen-containing bases and alkylene glycol-substituted calixarenes function to disperse sludge and/or neutralise acidic materials in lubricating oils.

Precursors of some at least of these compounds are known from a publication by V Bocchi, D Foina, A Pochini, R Ungaro and G D Andretti in Tetrahedron, Vol. 38, No. 3, pp 373 to 378 (1982) entitled "SYNTHESIS, $^1$H NMR, $^{13}$C NMR SPECTRA AND CONFORMATIONAL PREFERENCE OF OPEN CHAIN LIGANDS ON LIPOPHILIC MACROCYCLES". Described therein in relation to host-guest chemistry, transport phenomena and phase transfer catalysis are inter alia substituted calix[n] arenes of the formula:

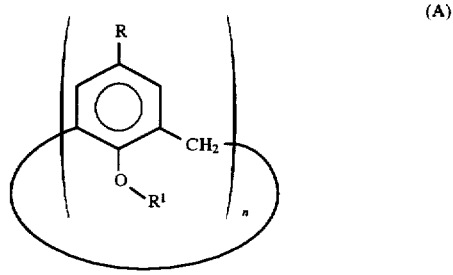

(A)

wherein either
n=4, R=tert-butyl and $R^1$=(CH$_2$CH$_2$O)$_2$CH$_3$;
or n=8, R=tert-butyl and $R^1$=CH$_3$;
or n=8, R=tert-butyl and $R^1$=CH$_2$CH$_2$OCH$_3$;
or n=8, R=tert-butyl and $R^1$=(CH$_2$CH$_2$O)$_2$CH$_3$;
or n=8, R=octyl and $R^1$=CH$_2$CH$_2$OCH$_3$;
or n=8, R=octyl and $R^1$=(CH$_2$CH$_2$O)$_2$CH$_3$.

In a publication by R Ungaro, A Pochini, G D Andreetti and P Domiano in the Journal of Inclusion Phenomena 3, 35–42, 1985 entitled "MOLECULAR INCLUSION IN FUNCTIONALIZED MACROCYCLES Part 10*: CRYSTAL AND MOLECULAR STRUCTURE OF A p-TERT-BUTYLCALIX[6]ARENE HEXAPODAND" the authors mention that a compound of the formula (A) wherein R=p-tert-butyl, $R^1$=CH$_2$CH$_2$OCH$_3$ and n=6 is superior to the calixarenes of the formula (A) wherein R=p-tert-butyl, $R^1$=CH$_2$CH$_2$OCH$_3$ and n=either 4 or 8 in the extraction of guanidinium, cesium and ammonium picrates from water to methylene chloride.

The present invention provides a compound comprised of a moiety derived from an organic nitrogen-containing base and a calixarene moiety in which the hydroxyl substituent (or substituents) is (are) substituted by oligoether chains.

The compound is suitably a complex of the moiety derived from an organic nitrogen-containing base and the calixarene moiety in which the hydroxyl substituent (or substituents) is (are) substituted by oligoether chains.

The compound may suitably be a complex of the formula (I):

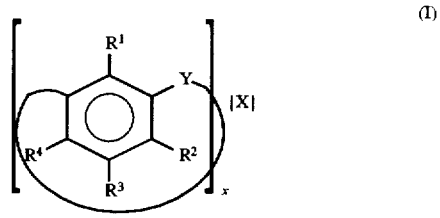

(I)

wherein Y is a divalent bridging group;

$R^3$ is hydrogen, hydrocarbyl or a hetero-substituted hydrocarbyl group;

either (1) $R^1$ is $OR^5$ and $R^2$ and $R^4$ are independently either hydrogen, hydrocarbyl or hetero-substituted hydrocarbyl, or (2) $R^1$ is either hydrogen, hydrocarbyl or hetero-substituted hydrocarbyl, and either both $R^2$ and $R^4$ are $OR^5$ or one of $R^2$ and $R^4$ is $OR^5$ and the other is —OH, $R^5$ being —(Z)$_n$R$^6$ in which Z is at least one alkylene oxide group, $R^6$ is hydrocarbyl or hetero-substituted hydrocarbyl and n is an integer in the range from 1 to 10; x is an integer in the range from 3 to 12; and X is a moiety derived from an organic nitrogen-containing base.

In the formula (I) the group Y may suitably be (CHR$^7$)$^{31}$$_y$ in which $R^7$ is either hydrogen or hydrocarbyl eg of 1–6 carbon atoms, such as methyl; y is an integer which is at least one; x is suitably from 4 to 9 and the group X is suitably a compound, for example a salt, derived from an organic nitrogen-containing base which is, for example guanidine or ammonium. Typically the salt may be a carbonate, a bicarbonate or a picrate. Thus X may be for example guanidinium carbonate.

A preferred compound has the formula (II):

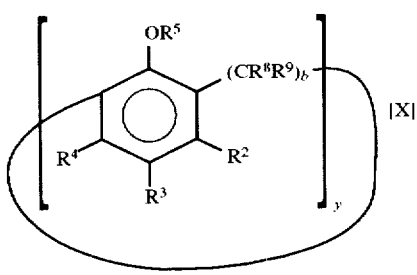
(II)

wherein $R^2$, $R^3$ and $R^4$ are independently either hydrogen, hydrocarbyl or hetero-substituted hydrocarbyl;

$R^5$ has the same meaning as in the formula (I);

either one of $R^8$ and $R^9$ is hydrogen and the other is hydrogen or hydrocarbyl;

y is an integer in the range from 4 to 9;

b is one or greater eg 1 to 4; and x has the same meaning as in the formula (I), eg of 1–20, such as 3–16 carbon atoms, more preferably alkyl; one of $R^8$ and $R^9$ is hydrogen and the other is either hydrogen or alkyl, for example methyl, more preferably $R^8$ and $R^9$ are both hydrogen; $R^5$ is —$(Z)_n R^6$ wherein Z is at least one of ethylene oxide (—$CH_2CH_2O$—), propylene oxide (—$CH(CH_3)CH_2O$—), butylene oxide, preferably ethylene oxide; $R^6$ is alkyl, preferably $C_1$ to $C_4$ alkyl, more preferably methyl and n is an integer from 2 to 6; y is 4, 6 or 8; b is one and X is a guanidinium salt.

$R^3$ is preferably alkyl, for example nonyl (or propylene trimer), t-butyl, dodecyl (or propylene tetramer) or tertiary-amyl.

Preferred compounds of the formula (II) are those in which $R^2=R^4=H$; $R^3=$t-butyl or dodecyl; $R^8=R^9=H$; $R^5=$($CH_2CH_2O)_2CH_3$; b=one; y=either 6 or 8 or a mixture thereof, eg 6, 8, and X is a guanidinium salt, for example guanidine carbonate.

A more preferred compound according to the present invention has the formula (III):

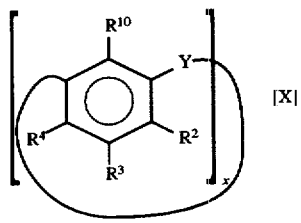
(III)

wherein $R^{10}$ is either hydrogen, a hydrocarbyl group or a hetero-substituted hydrocarbyl group;

either $R^2$ and $R^4$ are both —$OR^5$ or one of $R^2$ and $R^4$ is —$OR^5$ and the other is —OH;

$R^3$, $R^5$, Y, x and X have the same meanings as for the formulae (I) and (II).

Preferred compounds having the formula (III) are those in which $R^{10}$ is hydrogen, $R^3$ is hydrogen and Y is $(CHR^7)^{y'}$.

Compounds having the formula (III) are derived from calix resorcinarenes.

The compounds having the formula (I) may suitably be prepared by the steps of:

(A) reacting a metal base in a solvent therefor with a calixarene of the formula (IV):

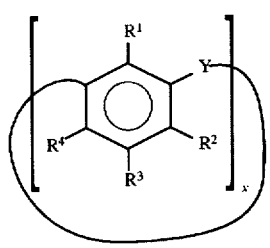
(IV)

wherein Y, and x have the same meaning as in the formula (I) either $R^1$ is hydroxyl and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or heterosubstituted hydrocarbyl to form the corresponding metal calixarate, (B) reacting the metal calixarate formed in step (A) with a compound having the formula (V):

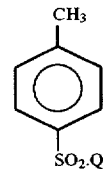
(V)

wherein Q is the group —$(Z)_n R^6$ in which Z, n and $R^6$ have the same meaning as in the formula (I) to form a compound having the formula (VI):

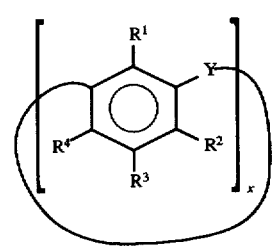
(VI)

wherein $R^1$, $R^2$, $R^3$, $R^4$, Y and x have the same meaning as in the formula (I), (C) complexing the compound having the formula (VI) with a compound X wherein X has the same meaning as in the formula (I) to form a compound of the formula (I), and (D) recovering the compound having the formula (I).

As regards step (A), calixarenes are well known compounds. For a review of calixarenes and their preparation the reader is referred to 'Monographs in Supramolecular Chemistry' by C. David Gutsche, Services Editor—J. Fraser Stoddart, published by the Royal Society of Chemistry, 1989. Typically, an alkyl phenol unsubstituted at the ortho-positions may be reacted in the presence of a base with an aldehyde, preferably formaldehyde in one or other of its forms, for example paraformaldehyde. Suitable calixarene starting materials include, for example p-tert butyl calix|8| arene, p-dodecylcalix|6,8| arene, p-dodecylcalix|6|arene, p-nonylcalix|8|arene, and the like. A preferred starting material is a calix|n|resorcinarene of the formula (IV) wherein Y, $R^1$ and x have the same meaning as in the formula (I) and $R^2$ and $R^4$ are hydroxyl, for example p-dodecylcalix|4| resorcinarene which may be prepared by reacting resorcinol in alcoholic solution. for example ethanol. in the presence of an acidic catalyst. for example aqueous hydrochloric acid. with dodecanal.

Whilst in step (A) any metal base may be reacted with the calixarene it is preferred to use either an alkali metal or an alkaline earth metal. preferably an alkali metal. base. Any basic compound of the metal. for example the oxide. hydroxide or alkoxide. may be employed. An example of a suitable metal base is potassium tert-butoxide. Suitably the calixarene and the metal base may be reacted at elevated temperature. for example a temperature in the range from 35° to 200° C.. typically from 40° to 100° C. The solvent may suitably be an oxygenated solvent. typically an ether. for example tetrahydrofuran.

In step (B) the metal calixarate formed in step (A) is reacted with a compound of the formula (V) to form a compound having the formula (VI). Compounds of the formula (V) may be termed oligoether tosylates. which are typically obtained by reacting the alcohol corresponding to the desired oligoether in the presence of an inert solvent and an organic nitrogeneous base. typically an amine. for example triethylamine. with a p-toluene sulphonyl (tosyl) halide. for example the chloride. Suitable solvents for the reaction include hydrocarbons and halohydrocarbons. for example dichloromethane.

In step (C) of the process the compound having the formula (VI) is used to complex a moiety derived from an organic nitrogen-containing base. typically a guanidine or ammonium. preferably a guanidine. salt. for example a carbonate. bicarbonate or picrate This is suitably accomplished by bringing together a solution of the compound having the formula (VI) in an inert organic solvent with an aqueous solution of the compound of the organic nitrogen-containing base. The two solutions are preferably well agitated such as by shaking together. stirring or other means. Suitable organic solvents include hydrocarbon solvents. for example toluene. The complexing may suitably be accomplished at room temperature.

In step (D) the compound having the formula (I) is recovered. This may be accomplished by any means known in the art. Typically in the method described hereinbefore the organic layer may be separated from the aqueous layer and the organic solvent separated therefrom to provide the complex.

The compounds hereinbefore described are suitable for use as ashless detergent additives in lubricating oil compositions.

Thus in another aspect the present invention provides a finished lubricating oil composition comprising a lubricating oil and at least one compound as hereinbefore described. the lubricating oil comprising greater than 90% by weight of the composition.

The lubricating oil may suitably be an animal. a vegetable or a mineral oil. Suitably the lubricating oil is a petroleum-derived lubricating oil. such as a naphthenic base. a paraffin base or a mixed base oil. Alternatively. the lubricating oil may be a synthetic lubricating oil. Suitable synthetic lubricating oils include synthetic ester lubricating oil. which oils include diesters such as di-octyl adiphate. di-octyl sebacate and tri-decyl adipate. or polymeric hydrocarbon lubricating oils. for example liquid polyisobutenes and poly-alphaolefins.

The finished lubricating oil composition may also contain effective amounts of one or more conventional lubricating oil additives. for example viscosity index improvers. anti-wear agents. antioxidants. dispersants. rust inhibitors. pour-point depressants. or the like.

The lubricating oil will provide greater than 90%. preferably greater than 95% by weight of the composition. The compound of the invention will suitably be present in a marine lubricating oil in an amount sufficient to provide a TBN in the range form 9 to 100 and in an automobile engine lubricating oil in an amount sufficient to provide a TBN in the range from 4 to 20.

Generally additive manufacturers market lubricating oil additives in the form of concentrates.

In yet another aspect the present invention provides an additive concentrate suitable for use in the production of finished lubricating oils which comprises at least one compound as hereinbefore described and a lubricating oil compatible solvent therefor. the compound comprising from 10 to 50% by weight of the concentrate.

As the lubricating oil compatible solvent there may be used a hydrocarbon solvent or mixture thereof. It is preferred to use as the solvent a lubricating oil. particularly a solvent neutral oil.

In addition to the compounds as described hereinbefore it is believed that certain of the intermediate compounds are also novel.

Thus in another aspect the present invention provides compounds of the formula (VI) as hereinbefore described other than those in which:

(i) x=4; $R^3$=t-butyl; $R^2$=$R^4$=H; $R^1$=O(CH$_2$CH$_2$O)$_2$CH$_3$ and Y=—CH$_2$—;

(ii) x=4; $R^3$=t-butyl; $R^2$=$R^4$=H; $R^1$=OCH$_2$CH$_2$OPh; and Y=CH$_2$—;

(iii) x=4; $R^3$=HSCH$_2$; $R^2$=$R^4$=H; $R^1$=O(CH$_3$CH$_2$O)$_2$H; and Y=CH$_2$—;

(iv) x=4–8; $R^3$=H or alkyl; $R^2$=$R^4$=H; $R^1$=O(CH$_2$CH$_2$O)$_{1-10}$H or O(CH$_2$CH$_2$O)$_{1-10}$ alkyl; and Y=—CH$_2$—;

(v) x=8; $R^3$=t-butyl; $R^2$=$R^4$=H; $R^1$=OCH$_2$CH$_2$OCH$_3$ and Y=—CH$_2$—;

(vi) x=8; $R^3$=t-butyl; $R^2$=$R^4$=H; $R^1$=O(CH$_2$CH$_2$O)$_2$CH$_3$ and Y=—CH$_2$—; vii) x=8; $R^3$=octyl; $R^2$=$R^4$=H; $R^1$=O(CH$_2$CH$_2$O)$_2$CH$_3$ and Y=—CH$_2$—; and (viii) x=8; $R^3$=octyl; $R^2$=$R^4$=H; $R^1$=OCH$_2$CH$_2$OCH$_3$ and Y=—CH$_2$—.

The invention will now be further illustrated by reference to the following Examples.

EXAMPLE 1

Preparation of p-dodecylcalix[4]resorcinarene methoxyethoxy ether/guanidine carbonate complex (A) Preparation of methoxy-ethoxyethoxy tosylate Methoxyethoxy ethanol (120.15 g. 1.0 moles. 1 equiv.). triethylamine (151.8 g. 1.5 moles. 1.5 equivs.) and dichloromethane (150 g. solvent) were charged into a 1 liter wide neck flask which was incorporated in an apparatus consisting of a flange lid. overhead stirrer and paddle. nitrogen inlet tube. condenser and calcium chloride drying tube and thermocouple/temperature readout.

The ingredients were stirred at room temperature under a nitrogen blanket and p-toluenesulphonyl (tosyl) chloride (209.7 g. 1.1 moles. 1.1 equivs.) was charged manually over 2 hours. An exotherm of 40° C. was noted over the period of addition. and the dichloromethane refluxed. The contents of the flask were left to stir overnight protected from the ingress of moisture by the CaCl$_2$ drying tube.

The reaction mixture was then poured into 500 ml ice-cold water. stirred and then separated. The aqueous layer was extracted with 2×250 ml dichloromethane and the organic layers were then combined. The combined organic layers were then washed with 2×250 ml ice-cold 2 Molar hydrochloric acid (aqueous) followed by 2×250 ml saturated sodium bicarbonate (aqueous). After washing the organic layer was separated, dried over anhydrous $MgSO_4$ and the $MgSO_4$ filtered off Solvent was removed on a rotavap at 40° C. and 29 inches Hg yielding a clear pale brown oil which slowly crystallised. The yield was 241.89 g corresponding to an 87% conversion.

The hydroxyl number of the starting material (methoxyethoxyethanol) was 322. The hydroxyl number of the product was zero. IR indicated the disappearance of the larger —OH peak at 3400 $cm^{-1}$ in the methoxyethoxyethanol starting material. Thus, from IR and hydroxyl number evidence the reaction was adjudged to be complete.

(B) Preparation of c-dodecylcalix|4|resorcinarene

A 5 liter round bottomed flange flask was charged with resorcinol (233.0 g, 2.12 moles, 1 equiv.), ethanol (774 ml, solvent) and 37% aqueous hydrochloric acid (258.0 g, 2.61 moles, 1.23 equivs.) It was then connected to a flange lid, stirrer (overhead) with paddle, pressure equalising dropping funnel and thermocouple. The reaction mixture was stirred until the resorcinol had dissolved (3 minutes) and then cooled to −10° C. with a butanol/solid carbon dioxide bath. Dodecanal (390.0 g, 2.12 moles, 1 equiv.) was then charged into the pressure equalising dropping funnel and added to the reaction mixture over 1 hour, after which time the temperature of the mixture had risen from −10° to −7° C. The cold bath was then removed.

The reactor contents were allowed to warm up to +7° C., the flask was placed into a mantle, and then the contents were heated to 85° C. After 3 hours at 85° C. the reaction mixture was in the form of a yellow semi-solid. The mixture was filtered through a porcelain Buchner funnel and the filter cake was washed with 500 ml ice cold water. The cake was then broken up and the fragments placed in porcelain evaporating dishes, which were placed in a fume cupboard for 2 days to dry the cake. The resulting yellow solid was broken up into a fine powder and stored. The yield was 469 g which represented an 80% conversion.

50 g of the product was recrystallised from methanol giving a bright yellow powder.

(C) Preparation of p-dodecylcalix|4|resorcinarene methoxyethoxyethoxy ether (MEE ether)

c-Dodecylcalix|4|resorcinarene obtained from (B) above (69.1 g, 0.25 moles, 1 equiv.) and dry tetrahydrofuran (350 g, solvent) were charged into a 1 liter wide neck round bottomed flask set up in an apparatus consisting of a flange lid, overhead stirrer and paddle, nitrogen inlet tube, condenser, calcium chloride ($CaCl_2$) drying tube, 500 ml pressure equalising dropping funnel and Eurotherm/thermocouple/mantle heating system. The mixture was stirred and heated to reflux (68° C.) under a nitrogen blanket. The mixture formed a clear blood-red solution. Potassium butoxide (70.24 g, 0.626 moles, 2.5 equivs.) was dissolved in dry tetrahydrofuran (300 g) and then added to the reaction mixture via the dropping funnel over three minutes. Heating was discontinued but reflux was maintained for 20 minutes by the exotherm. The flask contents were then allowed to cool to 60° C. over 10 minutes. The mixture remained clear and red.

Methoxyethoxyethoxy tosylate (from (A) above) (171.7 g, 0.626 moles, 2.5 moles) was dissolved in tetrahydrofuran (171.7 g, solvent) and added to the reaction mixture at 60° C. over 2 hours via the dropping funnel. No exotherm was observed but a reddish-brown precipitate appeared. 1 liter of water was added and the precipitate disappeared leaving a clear solution. The solution was divided into 2 portions and each was washed with 3×400 ml dichloromethane. The lower (green) layers were combined. The separation was good but it was necessary to shine a light through the funnel in order to clearly identify the interface because both layers were dark in colour. The combined lower layers were dried overnight over 4A molecular sieves and then the solvent was removed by a rotary evaporator (40° C., 28 inches Hg) to yield the product as a red oil. The yield was 389 g which corresponded to a 78% conversion.

(D) Preparation of guanidine carbonate/p-dodecylcalix|4|resorcinarene MEE ether complex The c-dodecylcalix|4|resorcinarene MEE ether obtained in (C) above was dissolved in toluene to give a 25% w/w solution and guanidine carbonate was dissolved in water to give a 25% w/w solution. 100 ml of each solution was added to a separating funnel and shaken vigorously for 1 minute. The emulsion was allowed to separate (took 1 minute) and the upper organic layer was separated and dried overnight over 4A molecular sieves. The toluene was then removed at 80° C./29 inches Hg on a rotary evaporator, yielding the complex.

The Alkalinity Value (AV) in terms of mgKOH/g was measured by the method of ASTM D2896 and an infra red spectrum was determined. From these determinations it was concluded that the AV was 50 and there were three guanidine molecules per ring.

EXAMPLE 2

Preparation of p-tert-butylcalix|8|arene MEE ether/guanidine carbonate complex (A) Preparation of methoxyethoxyethoxy (MEE) tosylate A portion of the MEE tosylate prepared in Example 1(A) was used.

(B) Preparation of p-tert-butylcalix|8|arene p-Tert-butylphenol (150.22 g, 1 mole, 1 equiv.), paraformaldehyde (60 g, 2 moles, 2 equivs.), 10M aqueous caustic soda (40 g, 0.4 moles, 0.4 equivs.) and xylene (2 kg, solvent) were charged to a 5 liter round bottomed flange flask and connected to a flange lid, overhead stirrer/paddle, Dean & Stark trap and condenser and mantle/Eurotherm/thermocouple heating system.

The reaction mixture was heated to 100° C. rapidly and then to 150° C. as distillation allowed (over 6 hours) and 50 mls of water was collected in the Dean and Stark trap. The mixture was refluxed for one hour after the last of the water was collected. By now the reaction mixture was in the form of a white suspension which was filtered through a porcelain Buchner funnel. The filter cake was dried in a vacuum oven at 40° C. and 25 inches Hg leaving a fine white powder. GPC analysis showed this to be very pure and in need of no further recrystallisation.

(C) Preparation of p-tert-butylcalix|8|arene MEE ether

The procedure described in Example 1 (C) was repeated except that the calixarene employed was the p-tert-butylcalix|8|arene prepared in (B) above (40.55 g, 0.25 moles, 1 equiv.) and the amounts of solvent tetrahydrofuran, MEE tosylate and potassium tert-butoxide were halved.

The product was a semicrystalline brown solid in an amount of 75 g corresponding to a 90% conversion.

(D) Preparation of p-tert-butylcalix|8|arene MEE ether/guanidine carbonate complex The procedure described in Example 1 (D) was repeated using the product obtained in (C) above.

The resulting complex had a TBN of 5 and an estimated number of guanidine molecules per ring of 0.3.

EXAMPLE 3

Preparation of p-dodecylcalix|6,8|arene MEE ether/guanidine carbonate complex (A) Preparation of methoxyethoxyethoxy (MEE) tosylate A portion of the MEE tosylate obtained in Example 1 (A) was employed.

(B) Preparation of p-dodecylcalix|6,8|arene

The procedure of Example 2(B) was repeated except that p-dodecyl phenol (95% para, ex. Schenectady, 262.44 g, 1 mole, 1 equiv.) was used in place of the p-tert-butyl phenol. The apparatus used and reaction conditions employed were otherwise identical. 65 mls of water were collected. The product remained soluble in the xylene and was decanted out of the apparatus leaving black grainy catalyst residues behind. The xylene was removed in a rotary evaporator at 90° C. and 28 inches Hg leaving the product as a brown clear glass which ground down into a mustard coloured powder. The yield was 244 g corresponding to an 89% conversion.

(C) Preparation of p-dodecylcalix|6.8|arene MEE ether

The procedure of Example 2(C) was repeated except that the calixarene used was p-dodecylcalix|6.8|arene obtained in (B) above (68.6 g, 0.25 mole, 1 equiv.). The product was a brown liquid in an amount of 71.4 g corresponding to a 75.7% yield.

(D) Preparation of p-dodecylcalix|6.8|arene MEE ether/ guanidine carbonate complex The procedure described in Example 1 (D) was repeated using the product obtained in (C) above.

The resulting complex had a TBN of 16.7 and the number of guanidines per ring was estimated to be one.

I claim:

1. A compound of the formula (III)

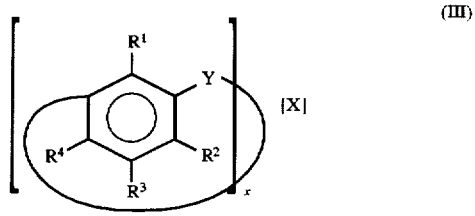

wherein $R^{10}$ is either hydrogen, a hydrocarbyl group or a hetero-substituted hydrocarbyl group; Y is a divalent bridging group;

either $R^2$ and $R^4$ are both —$OR^5$ or one of $R^2$ and $R^4$ is —$OR^5$ and the other is OH;

$R^3$ is hydrogen, hydrocarbyl or a hetero-substituted hydrocarbyl group;

$R^5$ is —$(Z)_nR^6$ in which Z is at least one alkylene oxide group, $R^6$ is hydrocarbyl or hetero-substituted hydrocarbyl and n is an integer in the range from 1 to 10;

x is an integer in the range from 3 to 12; and

X is a guadinium or ammonium salt.

2. A compound according to claim 1, wherein $R^{10}$ is hydrogen.

3. A compound according to claim 1, wherein $R^3$ is hydrogen.

4. A compound according to claim 1, wherein Y is (CHR$^7$)$_y$, wherein $R^7$ is either hydrogen or hydrocarbyl and y is an integer of at least 1.

5. A compound according to claim 4, wherein $R^7$ is hydrocarbyl of 1 to 6 carbon atoms.

6. A compound according to claim 1, wherein X is selected from the group consisting of a carbonate, a bicarbonate and a picrate salt.

7. A compound according to claim 6, wherein X is guanidinium carbonate.

8. A process for the production of a compound of formula (III) as defined in claim 1, which process comprises the steps of:

(A) reacting a metal base in a solvent therefor with a calixarene of the formula (IV)

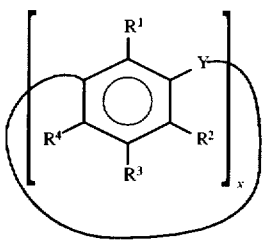

wherein Y is a divalent bridging group, x is an integer in the range of from 3 to 12, either $R^1$ is hydroxyl and $R^2$ and $R^4$ are independently either hydrogen, hydrocarbyl or hetero-substituted hydrocarbyl or $R^2$ and $R^4$ are hydroxyl and $R^1$ is either hydrogen, hydrocarbyl or hetero-substituted hydrocarbyl, to form the corresponding metal calixarate, (B) reacting the metal calixarate step formed in (A) with a compound having the formula (V)

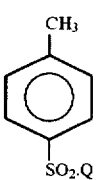

wherein Q is the group —$(Z)_nR^6$ in which Z is at least one alkylene oxide group, n is an integer in the range of from 1 to 10 and $R^6$ is hydrocarbyl or hetero-substituted hydrocarbyl, to form a compound having the formula (VI)

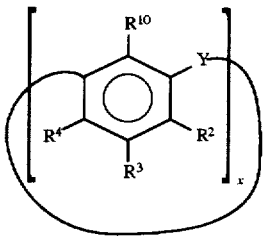

wherein $R^{10}$ is either hydrogen, a hydrocarbyl group or hetero-substituted hydrocarbyl group, either $R^2$ and $R^4$ are both —$OR^5$ or one of $R^2$ and $R^4$ is —$OR^5$ and the other is —OH, $R^3$ is hydrogen, hydrocarbyl or a hetero-substituted hydrocarbyl group, $R^5$ is —$(Z)_nR^6$ in which Z is at least one alkylene group, $R^6$ is hydrocarbyl or hetero-substituted hyrdrocarbyl and n is an integer in the range of from 1 to 10, and x is an integer in the range from 3 to 12.

(C) complexing the compound of formula (VI) with a compound (X), wherein X has the same meaning as above in connection with formula (III), and (D) recovering the compound having the formula (III).

9. An additive concentrate suitable for use in the production of finished lubricating oil compositions which comprises at least one compound as claimed in claim 1 and a lubricating oil compatible solvent therefor, the compound comprising from 10 to 50% by weight of the concentrate.

10. A finished lubricating oil composition comprising a lubricating oil and at least one compound as claimed in claim 1, the lubricating oil comprising greater than 90% by weight of the composition.

* * * * *